(12) United States Patent
Tarkeshian et al.

(10) Patent No.: US 9,205,186 B2
(45) Date of Patent: Dec. 8, 2015

(54) SYSTEM AND METHOD FOR PROVIDING PRESSURIZED INFUSION

(71) Applicant: Abbott Medical Optics Inc., Santa Ana, CA (US)

(72) Inventors: Branden Tarkeshian, Orange, CA (US); Mark E. Steen, Santa Ana, CA (US); James B. Gerg, Lake Forest, CA (US); Fred Lee, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 14/276,854

(22) Filed: May 13, 2014

(65) Prior Publication Data

US 2014/0276639 A1    Sep. 18, 2014

Related U.S. Application Data

(63) Continuation-in-part of application No. 13/829,926, filed on Mar. 14, 2013.

(51) Int. Cl.
| | | |
|---|---|---|
| *A61F 9/007* | (2006.01) | |
| *A61M 3/02* | (2006.01) | |
| *A61M 1/00* | (2006.01) | |

(52) U.S. Cl.
CPC .......... *A61M 3/0237* (2013.01); *A61M 3/0241* (2013.01); *A61M 3/0266* (2013.01); *A61F 9/00736* (2013.01); *A61F 9/00745* (2013.01); *A61M 1/0058* (2013.01); *A61M 2205/3331* (2013.01); *A61M 2205/502* (2013.01); *A61M 2210/0612* (2013.01)

(58) Field of Classification Search
CPC ............ F16M 13/00; A61F 2250/0068; A61F 9/00781; A61F 9/007; A61M 1/0058; A61M 2210/0612; A61M 3/0258; A61M 1/0023; A61M 1/0031
USPC ..................................... 604/35, 294
See application file for complete search history.

(56) References Cited

U.S. PATENT DOCUMENTS

| | | | | |
|---|---|---|---|---|
| 1,455,235 | A | * | 5/1923 | Townsend et al. ............ 222/109 |
| 2,208,550 | A | * | 7/1940 | Shapiro ........................ 604/405 |
| 2,373,124 | A | * | 4/1945 | Le Frank ...................... 222/307 |
| 2,413,710 | A | * | 1/1947 | Jason ............................ 222/333 |
| 2,716,517 | A | * | 8/1955 | Tollberg ....................... 141/117 |
| 2,954,806 | A | * | 10/1960 | Kerr .............................. 141/275 |
| 3,838,691 | A | * | 10/1974 | Paludan et al. ............... 604/323 |
| 3,973,602 | A | * | 8/1976 | Kruse ............................. 141/95 |
| 4,186,848 | A | * | 2/1980 | Walter ........................... 222/23 |
| 4,221,308 | A | * | 9/1980 | Goodall ........................ 222/478 |

(Continued)

FOREIGN PATENT DOCUMENTS

| | | |
|---|---|---|
| EP | 1428541 A2 | 6/2004 |
| WO | WO-0217833 A1 | 3/2002 |
| WO | WO-2009112251 A1 | 9/2009 |

OTHER PUBLICATIONS

International Search Report and Written Opinion for Application No. PCT/US2014/018568, mailed on May 9, 2014, 13 pages.

*Primary Examiner* — Scott Medway
(74) *Attorney, Agent, or Firm* — Abbott Medical Optics Inc.

(57) ABSTRACT

The present invention relates generally to providing pressurized infusion of liquids and more particularly, is directed to providing a stable and pressurized flow of irrigation fluid to the eye during surgery.

15 Claims, 7 Drawing Sheets

(56) References Cited

U.S. PATENT DOCUMENTS

| | | | |
|---|---|---|---|
| 4,343,824 A * | 8/1982 | Caldwell | 426/477 |
| 4,425,123 A * | 1/1984 | Di Salvo | 604/247 |
| 4,813,927 A * | 3/1989 | Morris et al. | 604/23 |
| 4,900,301 A * | 2/1990 | Morris et al. | 604/23 |
| 5,047,009 A * | 9/1991 | Morris et al. | 604/23 |
| 5,176,629 A * | 1/1993 | Kullas et al. | 604/31 |
| 5,234,038 A * | 8/1993 | Mitchell et al. | 141/293 |
| 5,341,836 A * | 8/1994 | Doherty | 137/268 |
| 5,403,276 A * | 4/1995 | Schechter et al. | 604/22 |
| 5,417,246 A * | 5/1995 | Perkins et al. | 137/870 |
| 5,563,584 A | 10/1996 | Rader et al. | |
| 5,810,765 A * | 9/1998 | Oda | 604/31 |
| 6,149,621 A * | 11/2000 | Makihara | 604/27 |
| 6,283,937 B1 * | 9/2001 | Takamatsu et al. | 604/31 |
| 6,391,000 B1 * | 5/2002 | Belikan et al. | 604/65 |
| 6,511,454 B1 * | 1/2003 | Nakao et al. | 604/31 |
| 6,527,745 B1 * | 3/2003 | Kanda et al. | 604/151 |
| 6,730,106 B2 * | 5/2004 | Kanda et al. | 606/171 |
| 6,780,166 B2 * | 8/2004 | Kanda et al. | 604/31 |
| 6,849,059 B2 * | 2/2005 | Suzuki et al. | 604/31 |
| 6,969,032 B2 * | 11/2005 | Olivera et al. | 248/176.1 |
| 7,563,242 B2 * | 7/2009 | Yaguchi et al. | 604/43 |
| 7,867,191 B2 * | 1/2011 | Suzuki | 604/35 |
| 8,070,712 B2 * | 12/2011 | Muri et al. | 604/30 |
| 8,287,486 B2 | 10/2012 | Injev | |
| 8,388,582 B2 * | 3/2013 | Eubanks et al. | 604/239 |
| 8,679,089 B2 * | 3/2014 | Berlin | 604/521 |
| 2003/0201412 A1 * | 10/2003 | Brody et al. | 251/5 |
| 2004/0108340 A1 * | 6/2004 | Witt | 222/464.3 |
| 2006/0100580 A1 * | 5/2006 | Muller | 604/152 |
| 2008/0033349 A1 * | 2/2008 | Suzuki | 604/35 |
| 2008/0114290 A1 * | 5/2008 | King et al. | 604/30 |
| 2010/0292631 A1 * | 11/2010 | Holden | 604/22 |
| 2011/0313343 A1 | 12/2011 | Milutinovic et al. | |
| 2013/0138035 A1 * | 5/2013 | Huculak et al. | 604/28 |

\* cited by examiner

SYSTEM AND METHOD FOR PROVIDING PRESSURIZED INFUSION

CROSS-REFERENCE TO RELATED APPLICATIONS

The present application claims priority to and is a continuation-in-part of U.S. patent application Ser. No. 13/629,926, filed Mar. 14, 2013, titled "System and Method for Providing Pressurized Infusion", the entirety of which incorporated by reference herein.

BACKGROUND OF THE INVENTION

1. Field of the Invention

The present invention relates generally to providing pressurized infusion of liquids and, more particularly, is directed to providing a stable and pressurized flow of irrigation fluid to the eye during surgery.

2. Description of the Background

Certain surgical procedures, such as phacoemulsification surgery, have been successfully employed in the treatment of certain ocular problems, such as cataracts. Phacoemulsification surgery utilizes a small corneal incision to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece or another handpiece, in a controlled manner. The surgeon may then insert a lens implant into the eye through the incision. The incision is allowed to heal, and the result for the patient is typically significantly improved eyesight.

As may be appreciated, the flow of fluid to and from a patient through a fluid infusion or extraction system, and thus the control of fluids and fluid pressure through the phacoemulsification handpiece, is critical to the procedure performed. Different medically recognized techniques have been utilized to control the fluid flow during the lens removal portion of the surgery. Among these, one popular technique is a simultaneous combination of phacoemulsification irrigation and aspiration using a single handpiece. This method includes making the incision, inserting the handheld surgical implement to emulsify the cataract or eye lens, and, simultaneously with this emulsification, having the handpiece provide a fluid for irrigation of the emulsified lens and a vacuum for aspiration of the emulsified lens and inserted fluids.

Currently available phacoemulsification systems, typically include a variable speed peristaltic pump and/or vacuum pump, a vacuum sensor, an adjustable source of ultrasonic power, and a programmable microprocessor with operator-selected presets for controlling aspiration rate, vacuum and ultrasonic power levels. The phacoemulsification handpiece is interconnected with a control console by an electric cable for powering and controlling a piezoelectric transducer that drives the action of the handpiece. Tubing provides irrigation fluid to the eye through the handpiece and enables withdrawal of aspiration fluid from an eye through the handpiece.

Generally, irrigation and aspiration are employed by the surgeon using the device to remove unwanted tissue and maintain pressure within the eye. Moreover, the use of, and particularly the infusion of, the irrigation fluid is critical and may, for example prevent the collapse of the eye during the removal of the emulsified lens. Irrigation fluid is also used to protect the eye from the heat generated by the ultrasonic cutting needle and may suspend fragments created during the surgery in fluid for more easy removal through aspiration.

Irrigation fluid has been conventionally handled in two ways. The first method to increase irrigation fluid pressure has relied upon the height of the fluid source. Conventional IV poles may be adjusted in height to create the sired pressure head using gravity-feed principles. The second method includes the use of an infusion pump, for either directly pumping the fluid and typically in the form of a peristaltic pump used in-line with an irrigation delivery line, or for pumping by pressurizing the fluid container to thus increase higher atmospheres above the fluid to thereby result in higher infusion pressure and flow to the surgical site.

Although each of the foregoing methods infuses irrigation fluid at the surgical site, each suffers from difficulties in maintaining a constant pressure. For example, infusion pumps must be deployed with a dynamic pressure-sensing control loop to prevent over or under pressurizing the anterior chamber, and may further require venting to control unwanted pressures. Solving these issues may require the use of a special drip spike, a mechanical pressurization compartment, or an over-bag, to control atmospheric pressure. Such solutions add costs and complications to the surgical set-up and to the maintenance of the surgical equipment.

Further, it is typical that the smaller the incision made during surgery, the greater the pressure needed to properly irrigate the surgical site, and gravity-feed systems may not produce the desired amount of pressure due at least to limitations on the height which may be achieved by physically raising the source of irrigation liquid. Typically, the irrigation source is mixed to a movable IV pole which is raised to increase the pressure head. Of course, limitations as to the maximum height of the IV pole and/or the height of overhead objects, such as lights or a ceiling, for example, may limit the amount of achievable height.

Thus, there is a need for a system and method that provides improved pressurized delivery of irrigation fluid to a surgical site.

SUMMARY OF THE INVENTION

The present invention is and includes a system and a method of providing pressurized fluid to the eye. The system and method may include at least one constant pressure source and at least one height adjustable irrigation fluid source to provide a stable pressurized fluid flow.

Accordingly, the disclosure provides a system and method that provides improved pressurized delivery of irrigation fluid to a surgical site.

DESCRIPTION OF THE DRAWINGS

The accompanying drawings are included to provide a further understanding of the invention, and are incorporated in and constitute a part of this specification. The drawings illustrate disclosed embodiments and/or aspects and together with the description, serve to explain the principles of the invention, the scope of which is determined by the claims.

In the drawings.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well-known in the art, and because they do not facilitate a better understanding of the present invention, a discussion of such elements and steps is not provided herein. The disclosure herein is directed to all such variations and modifications to the disclosed elements and methods known to those skilled in the art.

In an embodiment of the present invention, a pressurized line 140 is provided to an irrigation source 110, such as an IV bag/bottle, to increase the pressure within the irrigation source. This pressurization may be adjustable to maintain or increase irrigation pressure as needed, such as where sufficient height is unavailable to provide the necessary gravitationally forced pressure.

Figure 1:
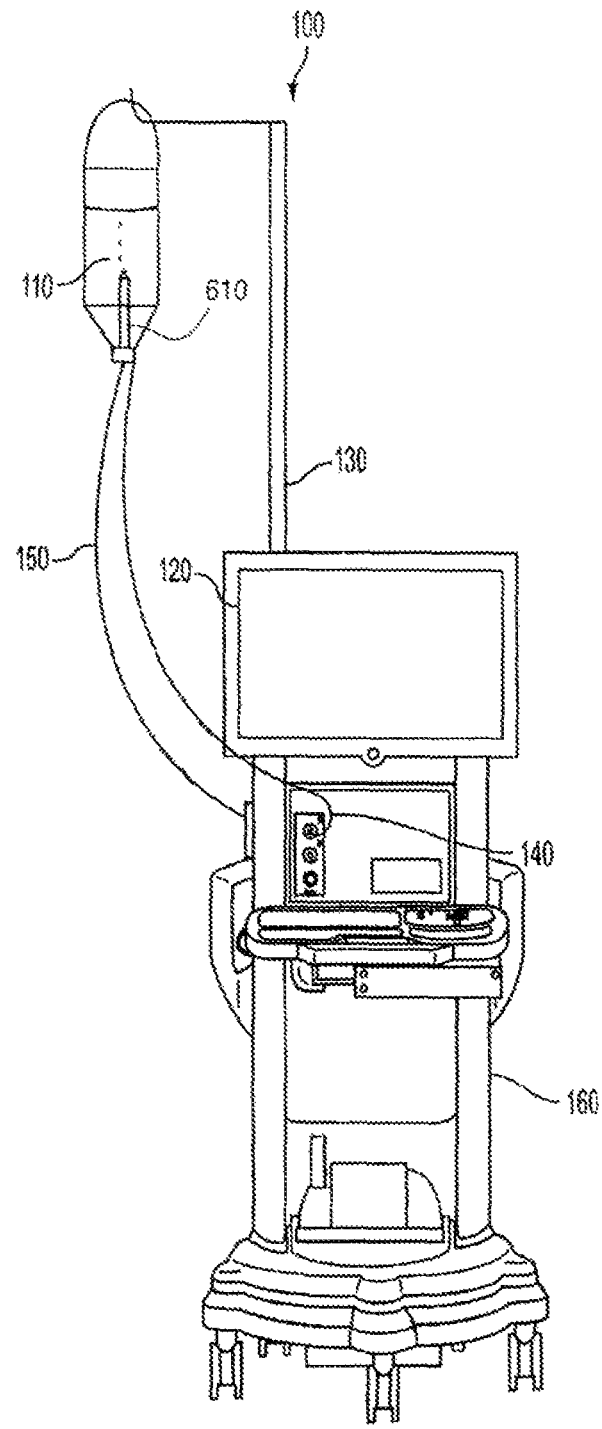
FIG. 1 illustrates an embodiment of the pressurized infusion apparatus of the present invention.

As illustrated in FIG. 1, a pressure supply line 140 may be provided from a surgical console 160 to at least one irrigation source 110. The pressure supply line 140 may provide any pressure desired by the user up to a maximum available pressure, and may use air or any specific gas to provide the increase or modification in pressure in at least the irrigation source 110.

The irrigation source 110 may the form of an IV bag for example, or may be or include any vessel used to hold irrigation fluid.

The pressure supply line 140 may be connected to the lower end of the irrigation source 110 such that pressurization of the irrigation source 110 is accomplished by the gas being delivered through the pressure supply line 140, whereupon the gas passes through a vent tube 502 (see FIG. 7) and into a pocket of gas above the irrigation fluid. Such a connection to the lower end of the irrigation source 110 may be made through an IV spike 610, for example. In this way, for example, the pressure supply line may be suitable for use with any size irrigation source.

Additionally and alternatively the pressure supply line 140 may terminate at the top, or highest point, within the irrigation source, to allow for the dispensing of the pressurized gas with little to no interaction with the body of the on fluid within the irrigation source 110. This form of delivery may decrease or eliminate the interaction of the delivered gas with the irrigation fluid, and may thus further decrease turbidity associated with the introduction of a pressurized gas.

Delivery of irrigation fluid may occur through a second line 150, which may begin at the lower end of the irrigation source 110 and may terminate at or into the surgical system controller 160 or run through the system controller 160 and terminate at a surgical handpiece (not shown). In an embodiment of the present invention, both the pressure supply line 140 and the irrigation delivery line 150 may be in fluidic communication with the irrigation source 110 through an IV spike 610. For example, the surgical system controller may include pressure fittings for each of the pressure supply line 140 and the irrigation delivery line 150. Further, an IV spike compatible for use with two lines may be constructed to withstand the increase in pressure provided by the system and may include valves or backflow prevention mechanisms to allow for reduction of pressure in, for example, the pressure supply line without the irrigation fluid entering the pressure supply line 140.

In an embodiment of the present invention, the pressurized gas may be limited to a low pressure or low maximum available pressure, and may be constant so as to provide a stable and non-dynamic pressure to the irrigation source. For example, the pressure delivered through the pressure supply line 140 may be set by a regulated air source which may have a range of 0 to about 5 PSI. As would be appreciated by those skilled in the art, a maximum available pressure may be controlled electronically or through limiting the size of the pressurization device which may be, for example, a compressor. Likewise, a threshold monitoring may be performed, or a metered pressurization, for example, to limit pressure below an acceptable maximum. The pressure resulting in the delivery line may be measured within the surgical system controller and may be controlled by a user of the system 100, as discussed herein.

In an embodiment of the present invention the resultant pressure within the irrigation delivery line 150 may thus be controlled by adjusting both the height of the irrigation source 110, the pressure introduced into the irrigation source 110 through the pressure supply line 140, or both. For example, an IV pole may be raised in conjunction with the addition of pressure into the irrigation source 110, to thereby increase the overall pressure of the fluid being delivered to the surgical system controller 160 and ultimately to the surgical site. Such a combination may allow for a more stable pressurized delivery of irrigation fluid by combining a constant minimum pressure through the pressure supply line 140 and dynamic pressure control through the changing of the irrigation source height. Such a blended approach may allow for more control over the pressure delivered during a surgical procedure, may reduce or eliminate unwanted pressure spikes or reduction in pressure due to vacuum buildup, and may allow for a reduced equipment zone by allowing for the use of shorter irrigation source heights, such as using a relatively short IV pole. Further, the increase of pressure which may be achievable using the present invention may provide the user with pressure sufficient to achieve a Tamponade feature if, for example, during surgery a retinal hemorrhaging arises.

In addition to the use of standard irrigation fluid sources such as, for example, IV bags/bottles, the present invention may also be suitable for use with other pressure delivery means, such as, for example, mechanically pressurized bags which may be equipped with a pressure transducer. Similarly, an irrigation source may be pre-pressurized (with the system allowing for a drop in pressure as the contents of the irrigation fluid are expelled). For example, as the pressure drops in a pre-pressurized irrigation fluid source, the height of the irrigation fluid source may be raised (either automatically or by indication to the graphical user interface discussed herein) to compensate and/or achieve the desired pressure. The height of the irrigation fluid source may be raised or lowered manually or using motorized means suitable for controlling the height and weight of such a pole.

Figure 2:
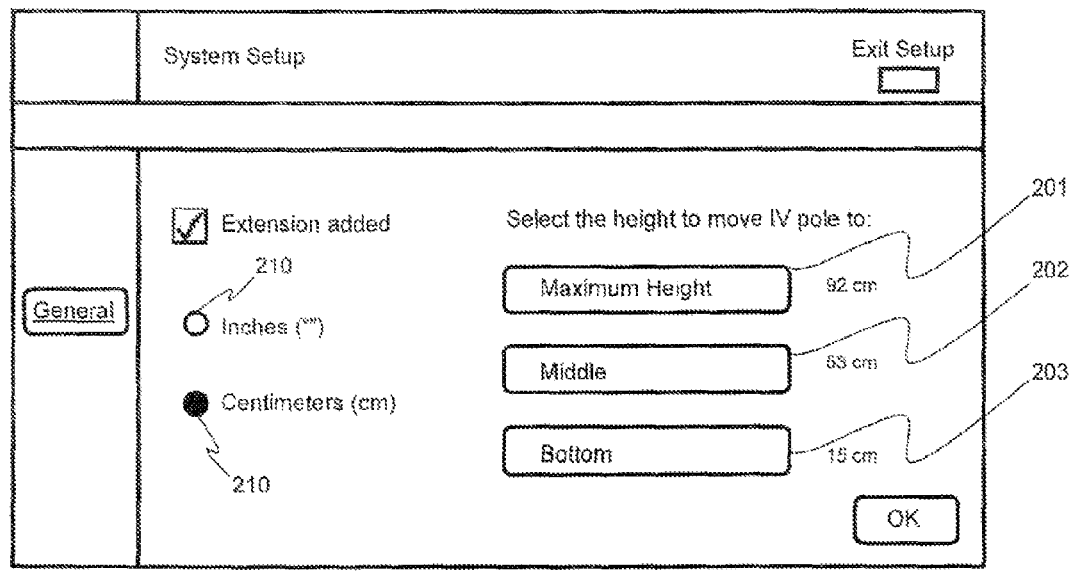
FIG. 2 illustrates an embodiment of the graphical user interface of the present invention.

The present invention may display the irrigation fluid pressure of the system on a graphical user interface (GUI) associated with the surgical system controller and be utilized through a touchscreen interface, for example. The GUI 200 may allow for the user to select, for example, an initial height of the irrigation source and/or may alert the user to the maximum and minimum heights achievable with the system. For example, as illustrated in FIG. 2, the system may allow for IV poles of various sizes and may be calibrated in regard to the maximum and minimum heights possible. Similarly, a middle or optimum height may be displayed for selection. Further, a use may select a predetermined height using one of buttons 201, 202, and/or 203. Such an optimal height may be, for example, a height at which a technician can easily access the irrigation source and which will also allow the system to provide the desired range of pressure.

As further illustrated in FIG. 2, the GUI 200 may present the user with options such as, for example, choosing the units of measurement used by the system. The height of the irrigation source may be selected to be displayed in inches using button 210 or centimeters using button 211 and may be converted into terms more common to a specific type of surgery. For example, when using the present invention in relation to an eye surgery, the pressure created by the height of the irrigation fluid may be translated into a more standard intraocular pressure (IOP) reading, in terms such as mmHg.

In an embodiment of the present invention, the pressure reading provided through the GUI may be indicative of the total pressure of the irrigation delivery line and may combine measurements of both the irrigation source height and the pressure provided into the pressure supply line. In this way, for example, the GUI may provide both an actual pressure reading based on direct measurement of the irrigation supply line, and a target or desired pressure based on the height of the irrigation fluid source and the pressure provided through the pressure supply line, if any.

Figure 3:
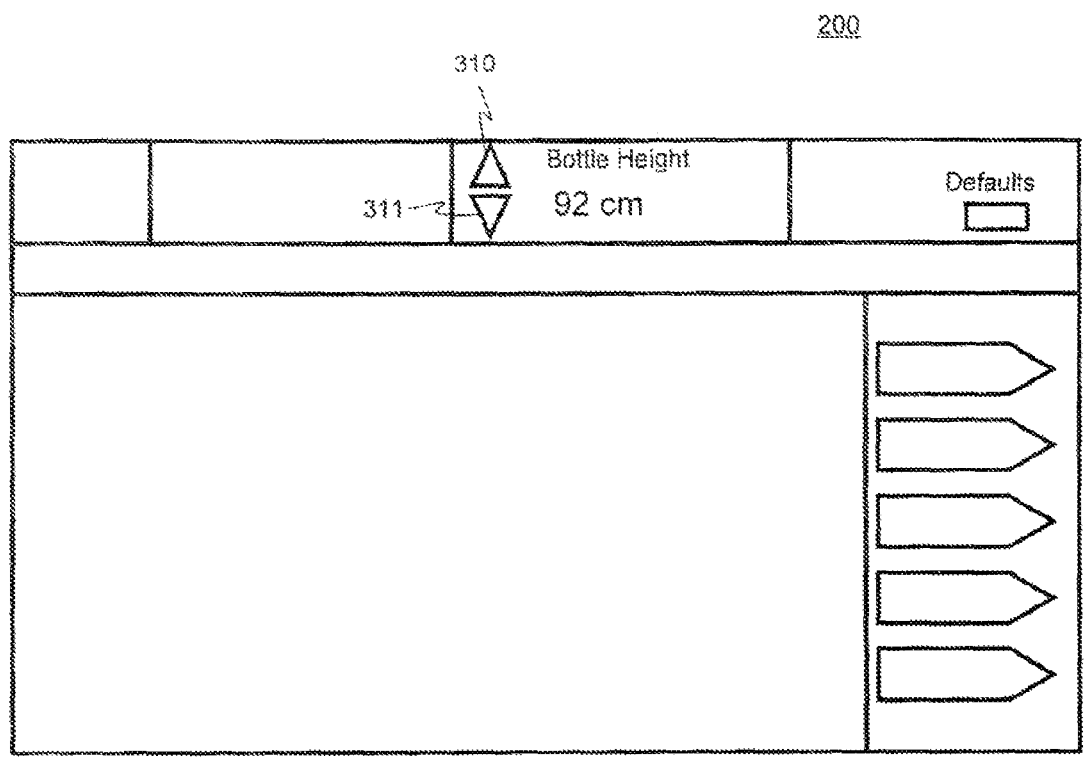
FIG. 3 illustrates an embodiment of the graphical user interface of the present invention.

As illustrated in FIG. 3, the GUI 200 may allow the user to adjust the pressure in the irrigation supply line by adjusting the height of the irrigation fluid source using buttons 310 and/or 311. The user may incrementally change the height, such as preferably altering the height in 1 cm increments. Further, the system may provide the user with certain preset pressure selections, which may respectively correlate to defined heights of the irrigation fluid source. For example, defined pressures may be given in 15 cm increments and may, for example, be given for heights such as 15 cm, 30 cm, 45 cm, and the like (not shown). Although any stepwise value may be used, the present invention may provide such predefined pressure heights to allow for ease of use and calibration of the system.

In a particular exemplary embodiment, the GUI 200 may provide a series of single-touch controls, for which an irrigation height of 30 cm may be one. If selected, the predefined pressure be expected to be a certain value, "X". If this value is not the value actually measured by the system in the pressure supply line, the system may reconfigure the assumed height value for the irrigation source, and/or may adjust the amount of secondary pressure being delivered into the pressure supply line.

Figure 4:
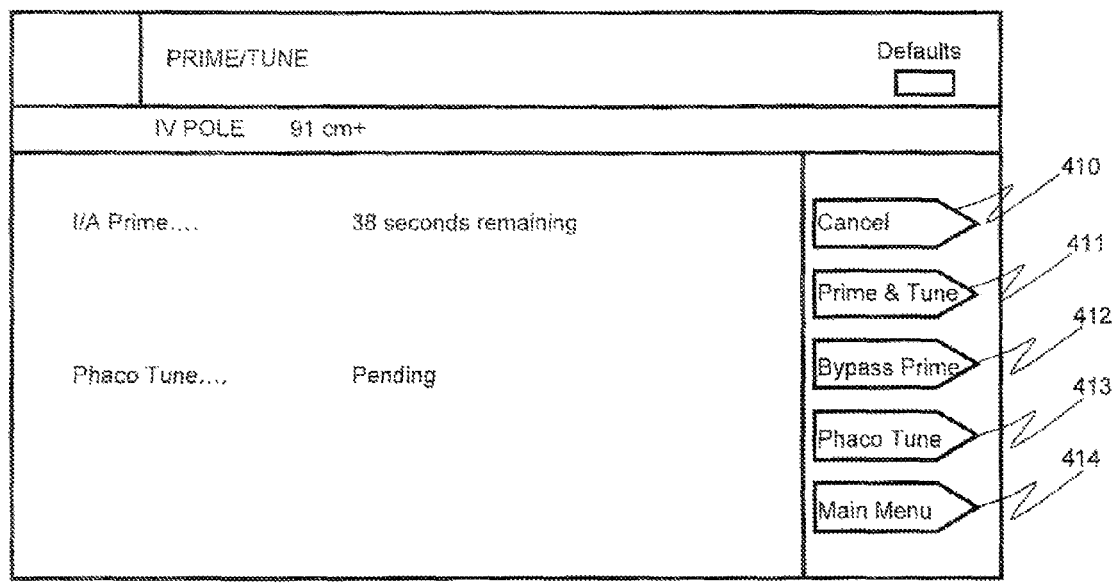
FIG. 4 illustrates an embodiment of the graphical user interface of the present invention.

As illustrated in FIG. 4, for example, the GUI 200 of the present invention may allow for the calibration and priming of the irrigating pressure. The GUI 200 may provide a time estimate for such calibration and may also provide the user with total irrigation source height information. By way of non-limiting example only, the GUI 200 may alert the user to a maximum height of 91+cm, which may be the total of the IV pole height (76 cm) and additional height by installation of an extension (15 cm).

The GUI 200 may also provide other options for the us such as, for example, allowing for canceling priming and tuning by selecting button 410, for example. Button 411 may allow the user to initiate priming and tuning of the system, while the Bypass Prime button 412 may allow for the priming feature to be passed over or aborted, for example.

In an embodiment of the present invention, a standard bottle/IV spike may comprise a vent lumen 505 suitable for allowing a vent tube to extend into an IV bottle and above the height of fluid contained in the IV bottle. The vent tube portion may be adjustable so as to accommodate various IV bottle sizes, heights and/or fluid levels. Use of a vent tube may allow for more control over the pressure of the irrigation fluid source. In this way, the pressurized delivery of irrigation fluid may be dynamically controlled and/or delivered to a surgical site.

Figure 5:
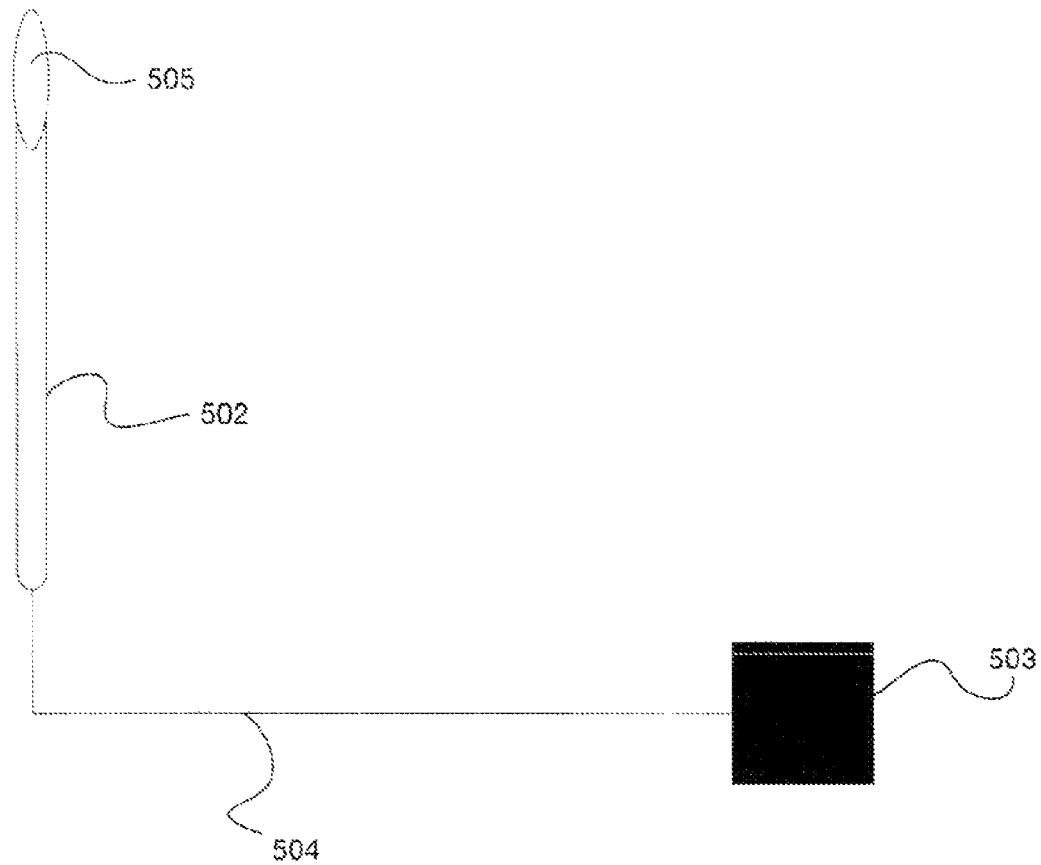
FIG. 5 illustrates an embodiment of the vent tube portion of the present invention.

As illustrated in FIG. 5, the vent tube 502 may be rigid and/or coiled for example, and may be foldable, such as using an accordion shape, for example, and may further be of any shape, such as circular and/or square, for example. A vent tube which is flexible and/or ribbed may allow for conformance to any irrigation source, such as, for example, an IV bag/bottle sizes. In an embodiment of the present invention, the vent tube 502 may include at least a portion which is threaded which may interface with a threaded portion of a vent lumen 505 and/or the IV spike.

In an embodiment, the height of vent tube 502 within irrigation source 110 may vary and may be adjusted based on many factors, including but not limited to a user's preference and the amount of fluid within the bottle or bag. The height of vent tube 502 within irrigation source 110 may be adjusted manually or automatically by system control based on pre-programmed or default system parameters. In an embodiment, the pressure within irrigation source 110 or the height of the irrigation source 110 may be adjusted manually or automatically by system control based on preprogrammed or default system parameters, including but not limited to flow rate, vacuum rate, pressure in the bottle or bag, pressure within an eye, whether there occlusion or partial occlusion at the handpiece, etc.

The vent tube 602 may further comprise a means of attachment 503 to at least one pressure source on system controller 160 through line 504. The at least one pressure source may allow for the increasing or decreasing of vacuum pressure through vent tube 502 in irrigation source 110. The use of those methods known to those skilled in the art may be used and may include, for example, Venturi-type pumps.

Figure 6:
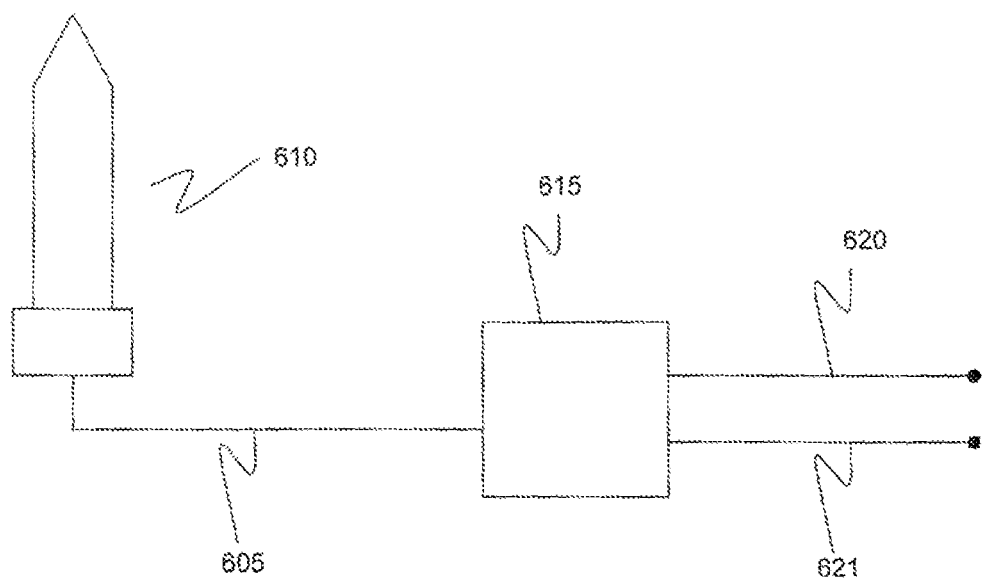
FIG. 6 illustrates an embodiment of the vent tube portion of the present invention.

As illustrated in FIG. 6 an IV spike apparatus may comprise a bottle spike 610, a vent lumen (not shown), an irrigation fluid receiving line 605, a tubing park 615, an aspiration line 620 and a fluid delivery line 621. The bottle spike 610 may be of common stock and may be suitable for use with known IV bags, for example. The tubing pack 615 may be designed to interact with existing medical systems, such as, for example, surgical system controller 160. The vent lumen may be an orifice near the bottom of the bottle spike 610 and may be self-sealing so as to allow for the insertion of the vent tube 502 into a pre-spiked IV bag. Alternatively, the vent tube 502 may be permanently affixed to the bottle spike 610 by at least, for example, a collar portion of the vent tube 502 which may allow for the height of the net tube 502 to be adjustable through at least a self-sealing portion.

Figure 7:
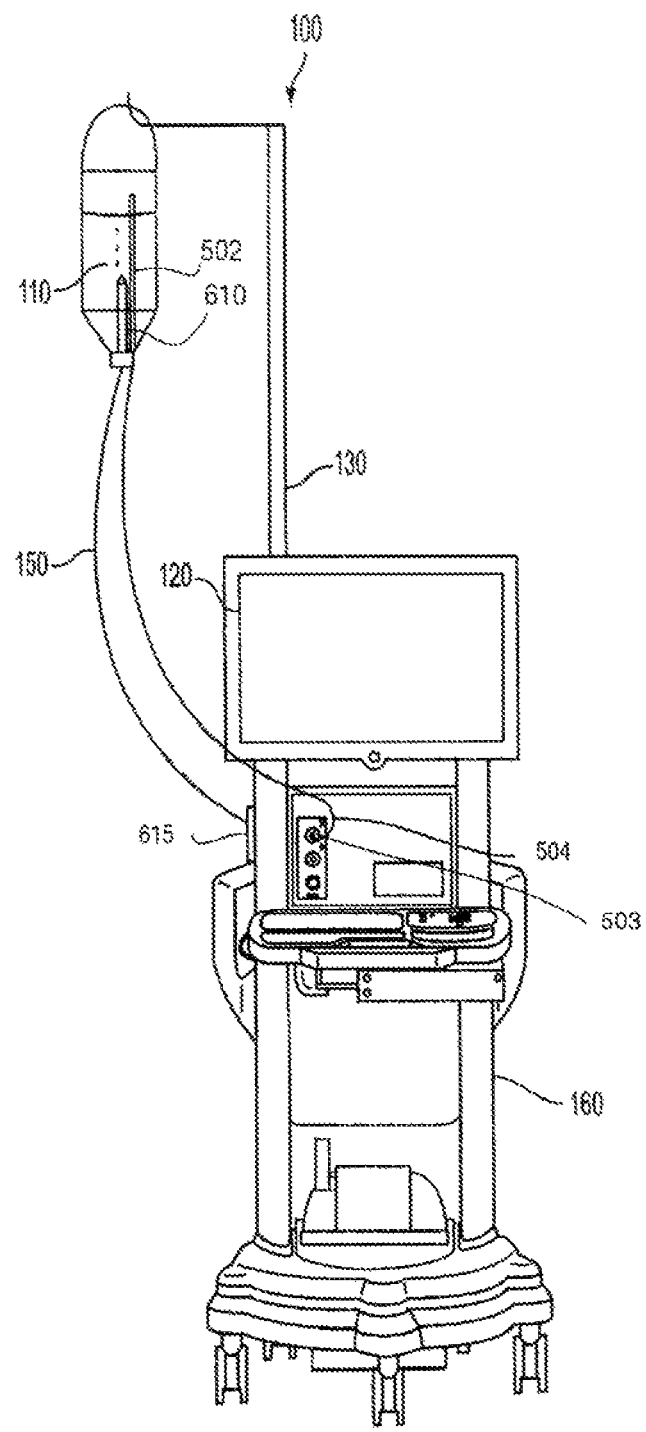
FIG. 7 illustrates an embodiment of the pressurized infusion apparatus of the present invention.

As illustrated in FIG. 7, when in use, the IV spike apparatus may be installed in an irrigation source 110 and the vent tube 502 may be inserted and/or raised through the vent lumen in the bottle spike 610. Attachment means 503 and/or tubing pack 615 may be operably attached to surgical system controller 160 where a controlled pressure may be delivered through line 504 to vent tube 502 to enable the pressurize regulation of irrigation source 110. For example, the vent tube 502 may allow for the reduction of pressure in the irrigation source 110 by venting air (not fluid) and/or may provide additional pressure to the irrigation source 110 by introducing air. In this way, the pressure within the irrigation source may be dynamically controlled at least through system controller 160, GUI 200, and/or footpedal.

Those of ordinary skill in the art may recognize that many modifications and variations of the herein disclosed systems and methods may be implemented without departing from the spirit or scope of the invention. Thus, it is intended that the present invention covers such modifications and variations provided they come within the scope the appended claims and their equivalents.

What is claimed is:

1. A system of providing pressurized fluid to the eye, comprising:
    at least one pressurized gas source communicatively coupled to at least one irrigation fluid source;
    at least one vent tube communicatively coupled to the at least one irrigation fluid source and the at least one pressurized gas source, wherein the at least one vent tube is disposed within the at least one fluid irrigation source; and
    a handpiece for dispensing irrigation fluid from the at least one irrigation fluid source at a desired pressure,
    wherein the desired pressure is partially regulated by adjusting the height of the at least one vent tube relative to the at least one fluid irrigation source.

2. The system of claim 1, further comprising:
    at least one pressure gauge for measuring the pressure of the dispensed irrigation fluid; and
    a controller for automatically regulating the pressure within the irrigation fluid source to approximate a target pressure.

3. The system of claim 2, further comprising:
    a controller for automatically adjusting a height of at least one pole suspending the at least one fluid irrigation source to an adjustable height relative to a floor or a patient to approximate the target pressure.

4. The system of claim 3, further comprising a valve suitable for maintaining the at least one pressurized gas source at a constant pressure.

5. The system of claim 3, wherein a pressure of the at least one pressurized gas source is from about 0 to about 5 psi.

6. The system of claim 2, wherein the at least one irrigation fluid source is selected from the group consisting of a bag or bottle.

7. The system of claim 3, wherein the adjustable height of the at least one pole suspending the at least one irrigation fluid source comprises an adjustment of at least one predetermined increment.

8. A method of providing pressurized fluid to the eye, comprising:
    providing at least one pressurized gas source communicatively coupled to at least one irrigation fluid source, wherein pressure in the at least one irrigation fluid source is configured to be dynamically adjusted;
    providing at least one vent tube communicatively coupled to the at least one pressurized gas source and the at least one irrigation fluid source, wherein the at least one vent tube is disposed within the at least one fluid irrigation source; and
    controlling the height of the at least one vent tube relative to the at least one fluid irrigation source to dynamically adjust the pressure in the at least on irrigation fluid source.

9. The method of claim 8, further comprising:
    measuring the pressure of the controlled gas; and
    adjusting the pressure of the at least one irrigation source to approximate a target pressure through the at least one vent tube.

10. The method of claim 9, wherein the adjusting is automatic.

11. The method of claim 8, further comprising:
    measuring the pressure of the controlled gas; and
    adjusting the pressure of the at least one irrigation source to approximate a target pressure by adjusting a height of the at least one irrigation source and the pressure in said at least one vent tube.

12. The method of claim 11, wherein the adjusting the pressure automatic.

13. The method of claim 8, further comprising maintaining the at least one pressurized gas source at a constant pressure.

14. The method of claim 8, wherein the pressure of the at least one pressurized gas source is from about 0 to about 5 psi.

15. The method of claim 8, wherein the at least one irrigation source is selected from the group consisting of a bag or bottle.

* * * * *